(12) United States Patent
Newton et al.

(10) Patent No.: US 9,179,966 B2
(45) Date of Patent: Nov. 10, 2015

(54) INSTRUMENT AND METHODS FOR ELECTRICAL CURRENT TREATMENT OF TISSUES AND METHODS FOR MONITORING THE SAME

(75) Inventors: Ronald Newton, Carson City, NV (US); Michael Cao, St. Petersburg, FL (US)

(73) Assignee: Vascular Technologies, Inc., Tampa, FL (US)

( * ) Notice: Subject to any disclaimer, the term of this patent is extended or adjusted under 35 U.S.C. 154(b) by 177 days.

(21) Appl. No.: 11/279,156

(22) Filed: Apr. 10, 2006

(65) Prior Publication Data

US 2006/0229595 A1    Oct. 12, 2006

Related U.S. Application Data

(60) Provisional application No. 60/669,866, filed on Apr. 8, 2005.

(51) Int. Cl.
*A61N 1/00* (2006.01)
*A61B 18/14* (2006.01)
*A61B 18/00* (2006.01)

(52) U.S. Cl.
CPC ....... *A61B 18/1485* (2013.01); *A61B 2018/005* (2013.01)

(58) Field of Classification Search
CPC ............. A61N 1/36128–1/36178; A61N 1/36; A61N 1/36021; A61N 1/36007; A61N 1/0512
USPC .................................. 607/39–47; 606/32–42
See application file for complete search history.

(56) References Cited

U.S. PATENT DOCUMENTS

| | | | | |
|---|---|---|---|---|
| 4,574,809 A | * | 3/1986 | Talish et al. | 607/27 |
| 4,898,169 A | * | 2/1990 | Norman et al. | 606/42 |
| 5,246,417 A | * | 9/1993 | Haak et al. | 604/20 |
| 5,817,138 A | * | 10/1998 | Suzuki | 607/67 |
| 2005/0267552 A1 | * | 12/2005 | Conquergood et al. | 607/96 |

* cited by examiner

*Primary Examiner* — Scott Getzow
(74) *Attorney, Agent, or Firm* — Timothy H. Van Dke; Beusse, Wolter, Sanks & Maire, PLLC (57) ABSTRACT

Disclosed herein are methods of delivering current to a target tissue using a medical instrument, wherein the medical instrument is configured to track and deliver a predetermined current time amount. Also disclosed herein are methods and a system of monitoring for usage of a hemorrhoid treatment instrument and invoicing for such usage.

8 Claims, 8 Drawing Sheets

INSTRUMENT AND METHODS FOR ELECTRICAL CURRENT TREATMENT OF TISSUES AND METHODS FOR MONITORING THE SAME

This application claims the benefit of U.S. Ser. No. 60/669,866 filed Apr. 8, 2005, under 35 USC §119(e) which is incorporated herein by reference.

BACKGROUND

It is estimated that one-third of the U.S. population has symptomatic internal hemorrhoids, with an incidence of 50% at age 50 years. Patients frequently postpone examination because of concern of pain associated with a particular treatment modality, hospitalization, cost, and time of disability. Such a delay in evaluation may lead to progression of the hemorrhoidal disease, or late diagnosis of more serious colorectal problems.

Medical procedures for hemorrhoidal treatment have taken many forms. For example, D.C. (direct current) management of hemorrhoidal disease was described in a review published by Wilbur E. Keesey, M.D. in 1934. The topical suppository approach is presently applied to a majority of patients, particularly those with a specific precipitating factor for hemorrhoidal disease (e.g., acute diarrhea episode) and in some instances may be all that is necessary. Necrosis and slough of hemorrhoidal vessels can also, at times, be accomplished by placement of rubber bands over the vessel base with a specific apparatus. This treatment is applicable to those vessels well above the pectinate line to avoid severe pain (a complication in 6 to 10% of patients). Mild to moderately diseased hemorrhoidal vessels are not amenable to this therapy. Injection sclerotherapy is effective for small (grade 1 and 2) bleeding internal hemorrhoids. Submucosal injection of sclerosant produces chemical thrombosis and fixation of the mucosa to the underlying tissue. Sclerotherapy of hemorrhoids is limited to mild to moderate disease and is associated with complications including reaction to the injected material, slough of the overlying mucosa, necrosis, and infection, including submucosal abcess. Cyrosurgery (i.e., application of a metal probe cooled by liquid nitrogen or carbon dioxide) freezes hemorrhoids. Occasionally, local anesthesia is required because of pain. Complications may include imprecise control of the depth of tissue destruction, post-operative pain, and rectal drainage. Surgical excision of hemorrhoidal inflammatory disease has the advantage of removing all associated redundant tissue, including the external component of a particular internal hemorrhoid. However, there are limitations to the amount of excision possible without major adverse sequelae. In a typical patient with many involved vessels, surgery can only approach the most symptomatic-diseased area and is not to be considered curative. The disadvantages of these approaches include pain, expense associated with hospitalization, time of disability, and potential complications, e.g., those associated with anesthesia, surgery proper, and post operative complications, including anal stenosis.

DETAILED DESCRIPTION

Figure 1:
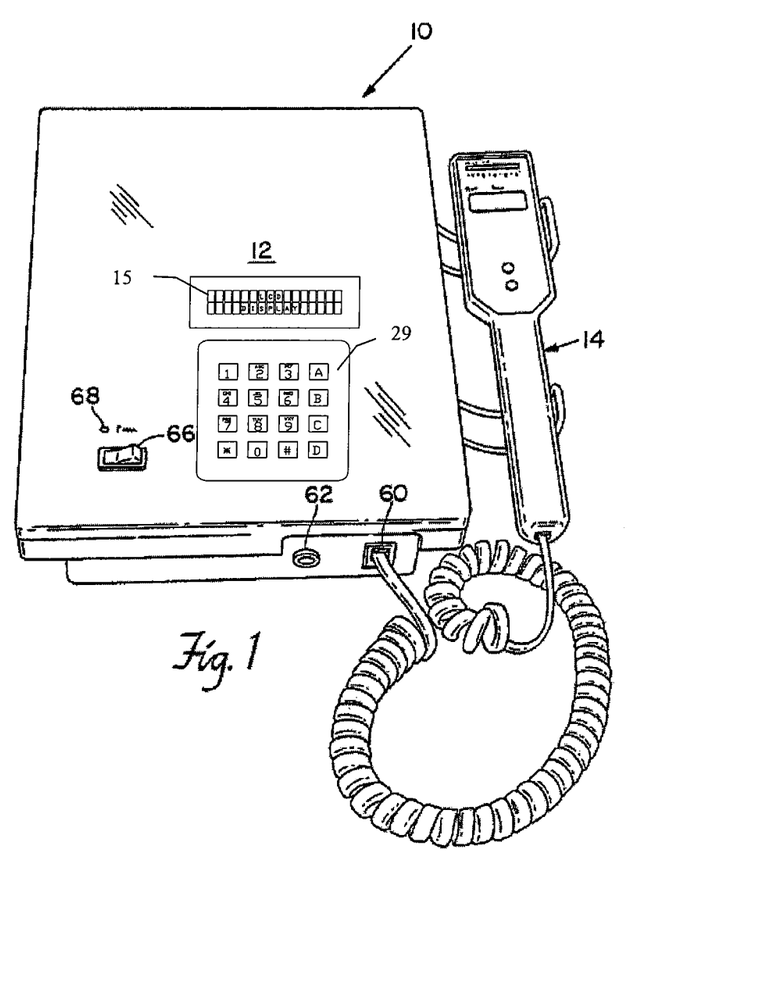
FIG. 1 is a perspective view of a medical instrument of the invention.

Referring to FIG. 1, the medical instrument 10 of the invention consists of a base unit 12 and a medical treatment handpiece 14. The instrument further consists of a monopolar, detachable probe and a grounding pad. Reference is made to U.S. Pat. No. 4,898,169 and co-pending U.S. patent application 60/652,587 whose teachings are incorporated herein in their entirety to the extent not inconsistent with the teachings herein.

Figure 2:
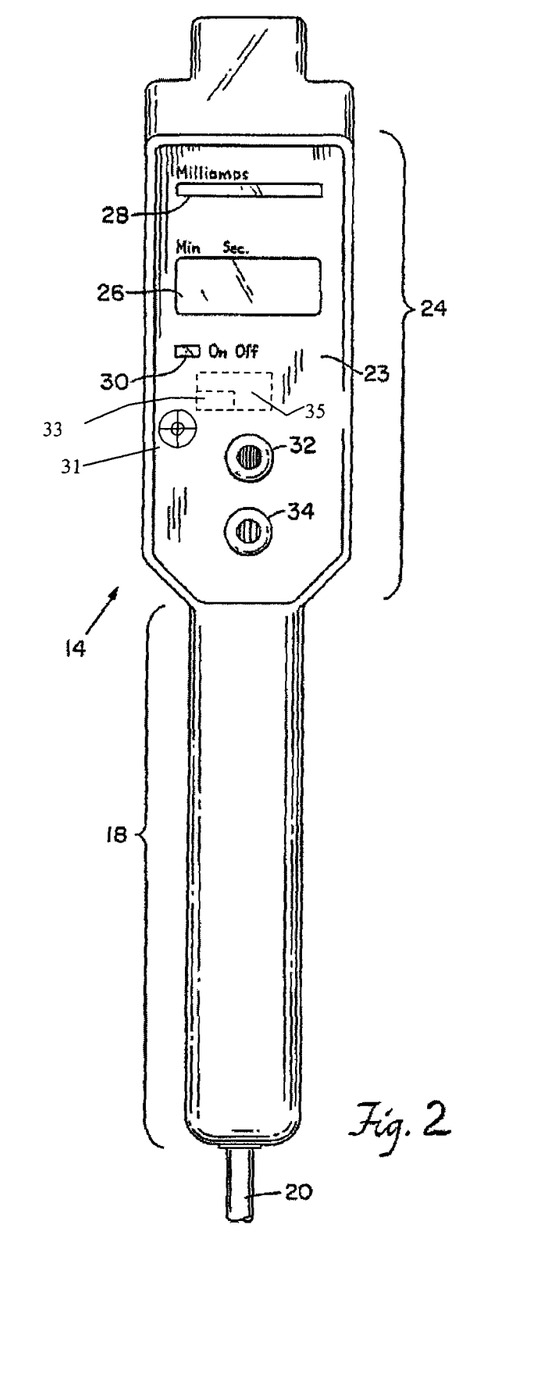
FIG. 2 is a plan view of the handpiece of FIG. 1.

Referring to FIG. 2, the handpiece 14 consists of a lower handle portion 18 from which extends a connector cord 20 to the base unit 12. The planar face surface 23 of the handpiece, on the upper patient treatment portion 24, contains display elements of, e.g., elapsed time of treatment (LED numeric display 26), level of treatment current (LED bar graph 28), and circuit status indicator (on/off display 30). In a specific embodiment, the LED numeric display 26 displays not the elapsed real time, but the handpiece 14 comprises program code modules to calculate the (current)×(time) for the treatment. This is typically provided in milliampere minutes. The upper patient treatment portion further contains switches 32, 34 for respectively incrementally increasing and decreasing the level of D.C. current through the probe and, when activated by the surgeon simultaneously, e.g., by pressing with his thumb, as described below, for ceasing flow of electricity. The handpiece face surface 23 is sealed against entry of fluid into the handpiece during cleaning between procedures. In addition, the inventors have realized that is unexpectedly helpful to configure the instrument 10 to monitor the cumulative current and time of a treatment session. At times, the current may fluctuate as a result, for example of the probe shifting during treatment. It is helpful to the user for the machine to track the current/time units of treatment session as a guideline for determining a medically sufficient application of current to the target tissue. Thus, the base unit 12 and/or the handpiece 14 is equipped with a processing module and program code module (represented, e.g., by 35 and 33, respectively, FIG. 2) to track the amount of current time units of a treatment session. Upon the treatment session reaching a predetermined amount of current time units, a visual indication is provided on the display 26, and/or an auditory signal is provided through speaker 31. Though not intended to supplant the user's judgment as to whether a sufficient treatment has been subjected to the target tissue, the tracking of current time units, and providing an indicator, is a helpful guide for facilitating a complete treatment of the target tissue, without overdoing the treatment.

Figure 7:
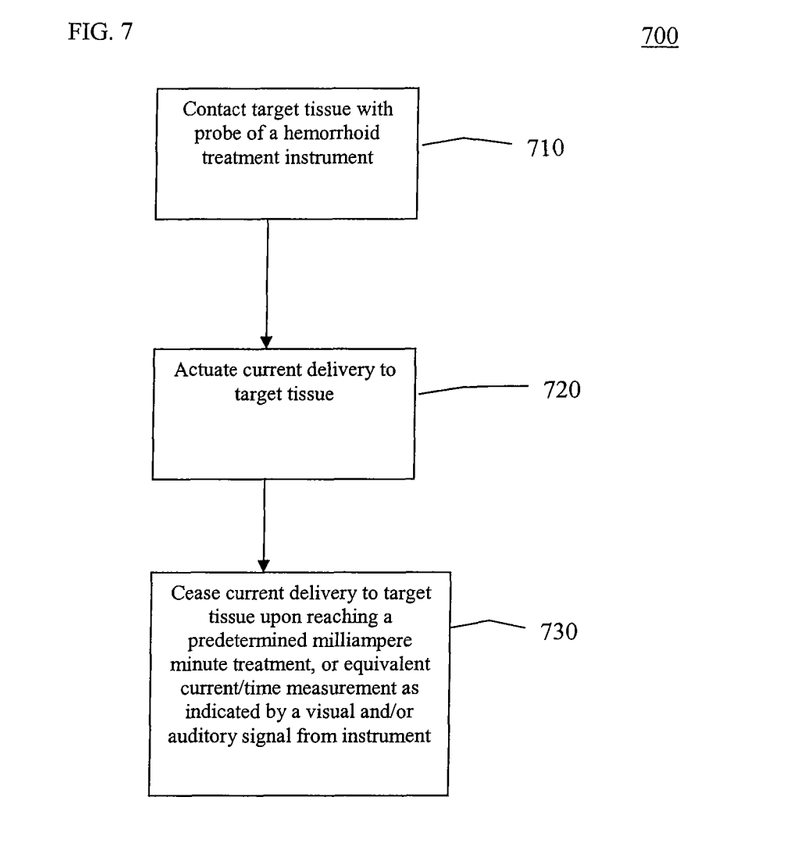
FIG. 7 a flow diagram of one treatment method embodiment of the invention.

FIG. 7 is a flow diagram of one method embodiment 700 of treating a target tissue. In a first step, a target tissue is contacted with a probe of a current delivering medical instrument 710. Upon contact, the instrument is actuated to deliver current to the target tissue 720. At a point when a predetermined current time unit amount is achieved, a visual and/or auditory indication is provided to the user 730. The indication provides valuable feedback to the user to assist in determining whether the target tissue has been sufficiently treated. Typically, the visual or auditory indication will dictate that the treatment be ceased, but not in all cases. The current delivery may be automatically terminated upon reaching the predetermined current/time unit amount, or may continue until it is manually terminated by the user of the instrument.

Figure 8:
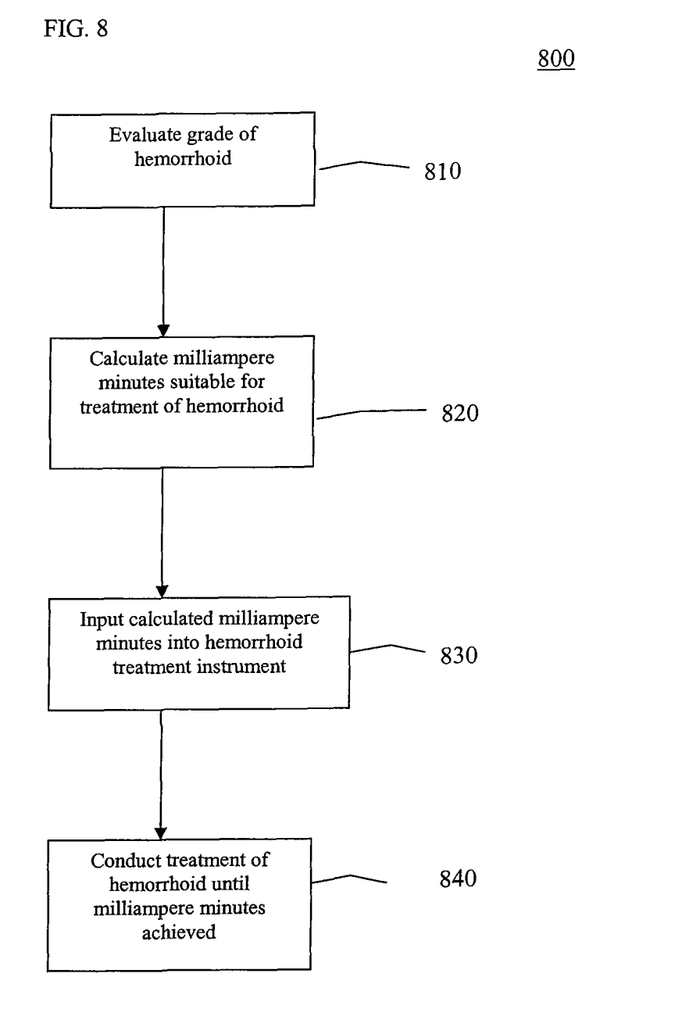
FIG. 8 a flow diagram of one treatment method embodiment of the invention.

FIG. 8 represents a flow diagram of a more specific treatment embodiment 800. It is known that depending on the characteristics of a particular hemorrhoid, the hemorrhoid may be categorized to be a certain grade of hemorrhoid. In a first step 810, the grade of a target hemorrhoid is determined. The amount of current/time units is calculated based on the grade of the hemorrhoid 820. The decided current/time units is inputted into the 830. Treatment of the hemorrhoid is conducted at least until the predetermined current/time units (in this case milliampere minutes) is achieved 840. The calculating of the appropriate current/time units may be conducted manually, or may be conducted via a calculation means provided on the instrument. The inputting of the appropriate current/time units may be manually inputted into the instrument or may be automatically selectable by the instrument, wherein inputting is an automatic step. Alternatively, the instrument has preconfigured modes correlating with different grades of hemorrhoids that are selectable by the user.

According to another embodiment, the subject invention pertains to a method of monitoring and billing for usage of a hemorrhoid treatment instrument. The instrument may be remotely coupled to computer associated with a billing party through a data communication network. In one embodiment, the instrument may transmit information to a billing party indicative of an amount of usage of the instrument over a billing period. In response to receiving usage information, the billing party may determine an invoice amount and initiate the printing of an invoice at a billing destination. In another embodiment, the instrument determines an invoice amount based upon the usage information and causes an invoice with the invoice amount to be printed.

Figure 3:
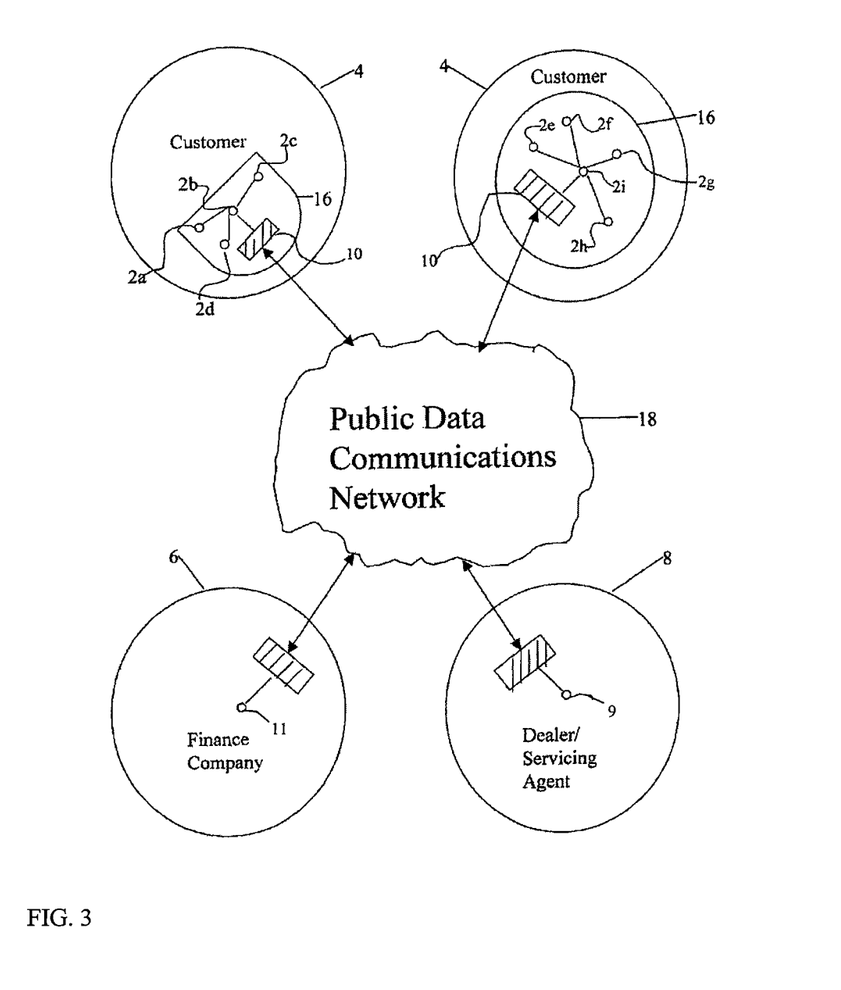
FIG. 3 is a diagram of a billing system embodiment based on usage of a medical instrument.

FIG. 3 shows a topology of a network coupling a medical customer with a finance company 6 and a dealer or servicing agent 8. It should be understood that the finance company 6 and the dealer or servicing agent 8 may be the same party. A medical customer premises 4 includes one or more instruments 2 coupled to a data communications network 18. Additionally, the instrument 2 may be located off of a customer's premises and coupled to a data communication network via a hardwired or wireless link. A dealer/servicing agent 8 may include entities which are contracted to service or maintain one or more of the instruments 2. A finance company 6 may include entities which are in the business of purchasing instruments 2 which are then leased to the medical customers for use. Such lease terms may specify periodic payments to be made by the medical customer to the finance company 6 either directly or through the dealer/servicing agent 8. Here, the medical customer may receive a periodic statement providing an invoice amount for the lease during a relevant billing period, and may indicate how the invoice amount was determined. In one embodiment, the invoice amount for the lease of any particular instrument 2 may be based upon a measure of usage of the particular instrument 2 over the relevant billing period.

FIG. 3 shows that instruments 2 at a medical customer premises 4 may be coupled together in a local area network (LAN) 16. Each LAN 16 includes a firewall 10 which enables communication between the instruments 2 and other nodes in a public data communication network 18 such as the Internet. Similarly, the dealer/servicing agent 8 and the finance company 6 may also have hosts 9 and 11 which are capable of communicating with devices coupled to the public data communications network 18. It should be understood that other suitable public or private data communication networks, and combinations of public and private networks, may be used to facilitate communication between and among the hosts 11 and 9, and the instruments 2.

In the illustrated embodiment, the instruments 2 may include processing module(s) and program code modules configured for maintaining information representative of a measure of usage of the device over the billing period. For example, the instrument 2 may include a program code module for counting a number of milliampere minutes, or number of treatment sessions. The instrument 2 may also include a network controller capable of supporting communication through an Ethernet port coupled to the LAN 16. In alternative embodiments, the devices 2 may be coupled in the LAN 16 with wireless links. The Ethernet controller may allow the instruments to be configured to perform as Internet devices according to an Internet Protocol (IP). Connection of the instrument 2 to a LAN or WAN may also be accomplished through a universal serial bus port.

In an alternative embodiment, a controller (not shown) external to the instrument 2 may maintain the usage information. For example, the instrument 2 may transmit a signal to the external controller upon usage events, such as, but not limited to, milliampere minutes or some other time unit of activity.

In another embodiment, particular instruments 2 may include a telephone modem enabling communication to either the finance company 6 or the dealer/servicing agent 8 through a point to point dial-up connection.

In the presently illustrated embodiment, the host 12 at the finance company 6 and the host 14 at the dealer/servicing agent 8 may execute one or more processes for communicating with individual instruments 2 to the public data communication network 18 using one or more protocols supported by the public data communication network 18. The finance company 6 or dealer/servicing agent 8 may individually or collectively serve as a "billing party" which maintains information related to periodic invoices to be provided to the customers for usage of one ore more of the instruments 2. As discussed below, processes associated with the billing party (e.g., processes executing on one or more of the hosts 12 and 14) may interact with the instruments 2 for the automated generation of human readable invoices (e.g., printed from or displayed at the instruments 2) at the customer premises 4. U.S. Patent Application No. 20010037270 is cited herein in its entirety to the extent not inconsistent with the teachings herein for alternate billing embodiments based on usage of the hemorrhoid treatment instrument.

Figure 4:
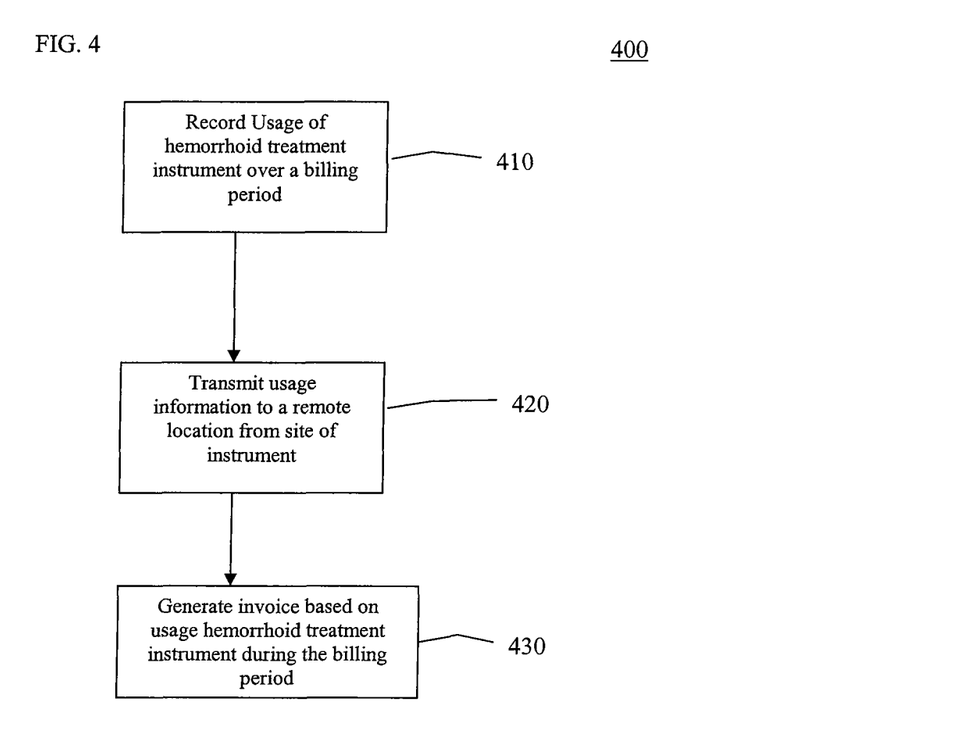
FIG. 4 flow diagram representing a method for billing for usage of a medical instrument.

FIG. 4 represents a flow diagram of a method 400 of invoicing for usage of a hemorrhoid treatment instrument. In a first step 410, usage of the hemorrhoid treatment instrument is recorded. This may be with accomplished by a processing module and program code module provided in the instrument. This may be accomplished by a conventional analog rotating counter that rotates as a function of current/time usage of the instrument. In a second step, the usage information is transmitted to a remote location. This may be accomplished by the instrument electrically transmitted information over a direct person to person phone connection or via a network system such as the internet. The instrument may transmit this information to the remote location directly or transmit to another device on site with the instrument that then transmits the information to the remote location. In an alternative embodiment, the information may be manually or verbally transmitted from a person noting the usage information to a person or machine at the remote location. This may be prompted by a person or machine at the remote location by a periodic and/or regularly scheduled contacting of a person or machine at the site of the hemorrhoid treatment instrument. In another step 430, an invoice is generated based on the usage information.

The term "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information.

As will be appreciated by one of skill in the art, embodiments of the present invention may be embodied as a device, method, or system comprising a processing module, and/or computer program product comprising at least one program code module. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, DVDs, optical storage devices, or magnetic storage devices.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of certain embodiments of the present invention may be written in an object oriented and/or conventional procedural programming languages including, but not limited to, Java, Smalltalk, Linux, Unix, "C", FORTRAN, or C++. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain embodiments of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer-readable program code modules. These program code modules may be provided to a processing module of a general purpose computer, special purpose computer, embedded processor or other programmable data processing apparatus to produce a machine, such that the program code modules, which execute via the processing module of the computer or other programmable data processing apparatus, create means for implementing the functions specified in the flowchart and/or block diagram block or blocks.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

Figure 5:
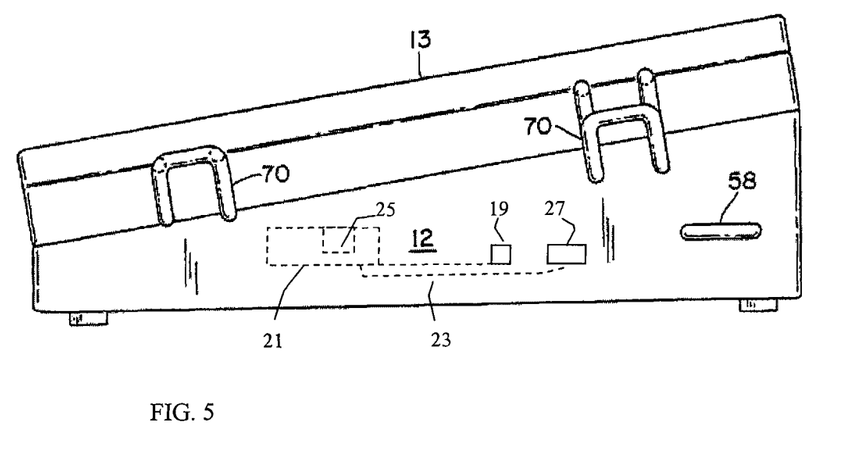
FIG. 5 is a side view of the instrument base unit.

Referring again to FIG. 1 and to FIG. 5, the base unit 12 includes a connection 58 for a power cord, an outlet 60 for connection to a handpiece cord and an outlet for connection to a grounding unit cord (not shown). On the face surface 13 of the base unit 12, there is an on off switch 66, and a light element 68 for indicating actuation of the instrument. Extending from the side of the base are a pair of brackets 70 for receiving the handpiece. In an alternative embodiment, the base unit 12 further comprises a universal serial bus port 27 and a telephone jack 19. Those skilled in the art will appreciate that the outlets and jacks may be positioned at any convenient location on the unit 12. The base unit 12 comprises circuitry 23, processing module(s) 21 and program code module(s) 25 configured such that information concerning use of the unit may be transmitted to a computer (not shown) on the user's site or to a remote location via a telephone or network communication. Furthermore, the face 13 of the base unit 12 comprises a numerical touch pad 29 for inputting information pertaining to use of machine or for inputting telephone numbers and a display 15.

Figure 6:
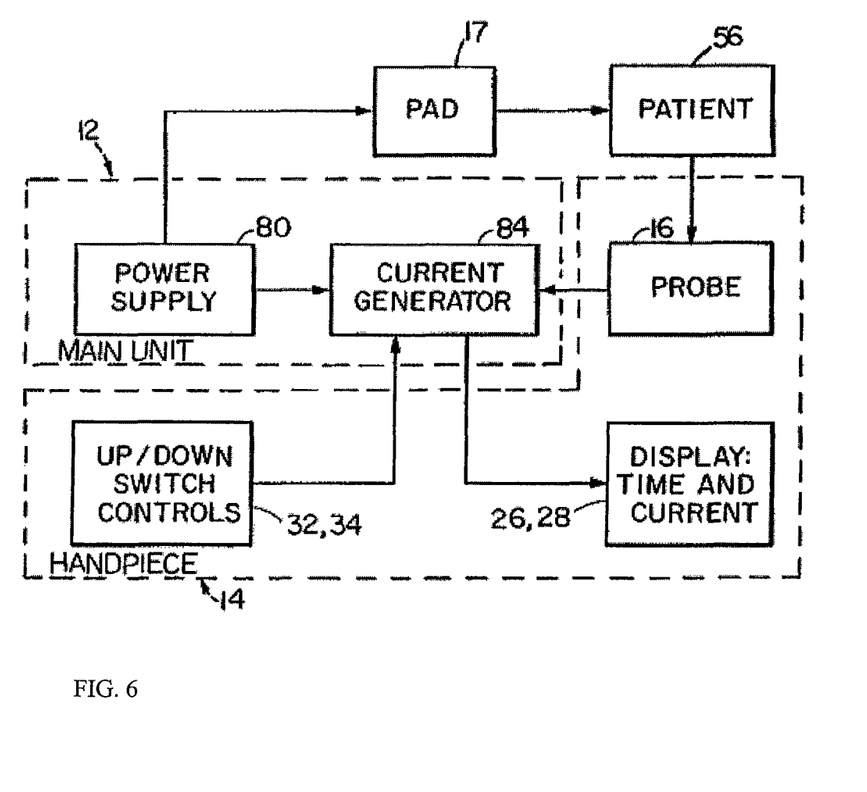
FIG. 6 a block diagram of an embodiment of the invention.

Referring to FIG. 6, the medical instrument consist of three electrical components; a main unit 12, a hand piece 14 and a pad 17. The main unit is comprised of a power supply 80 and a current generator 84. The power supply 80 provides D.C. voltage to logic circuitry of the switch controls 32, 34, the time and current display 26, 28 and the ground pad 17. The current generator 84 is connected to the probe 16 and is used for controlling electrical D.C. current that is to be transmitted from the pad 17 through the patient 56 to the probe 16. In handpiece 14, switches 32, 34 positioned on the handle of the probe are connected to the current generator 84 for incremental adjustment of the current transmitted through the patient 56. Digital circuitry components, connected to the current generator 84 and placed on the handle of the probe, enable a visual display 26, 28 of the quantity of current transmitted and elapsed time of treatment, such as in milliampere minutes.

Finally, while various embodiments of the present invention have been shown and described herein, it will be obvious that such embodiments are provided by way of example only.

Numerous variations, changes and substitutions may be made without departing from the invention herein. The teachings of all patents and other references cited herein are incorporated herein by reference to the extent they are not inconsistent with the teachings herein.

What is claimed is:

1. A method of treating a hemorrhoid comprising:
    inputting a predetermined current time unit into a current delivering medical instrument, wherein the predetermined current time unit is based on grade of the hemorrhoid;
    contacting said hemorrhoid with a probe of the current delivering medical instrument;
    delivering current to the hemorrhoid; and
    determining a delivered current time unit, said delivered current time unit comprising a product comprised of current delivered multiplied by time,
    providing a visual and/or auditory indication with the medical instrument when the predetermined current time unit amount is achieved.

2. The method of claim 1, wherein said medical instrument is configured to terminate current delivery automatically upon achievement of said predetermined current time amount.

3. The method of claim 1, wherein current delivery is manually terminated by a user of the instrument.

4. A method of treating a hemorrhoid with a current delivering medical instrument that includes a probe, a speaker, and a microprocessor, the method comprising the following steps:
    contacting said hemorrhoid with the probe of the current delivering medical instrument;
    delivering current to the hemorrhoid via the probe;
    determining by the microprocessor a delivered current time unit, said delivered current time unit comprising a product comprised of current delivered multiplied by time; and
    producing an auditory indication through the speaker after the expiration of a predetermined current time unit, said predetermined current time unit based on a grade of the hemorrhoid.

5. The method of claim 4 including the additional step of ceasing delivery of current after the expiration of the predetermined current time unit.

6. A method of treating a hemorrhoid comprising the following steps:
    selecting a preconfigured mode in a current delivering medical instrument, wherein the preconfigured mode corresponds to a grade of the hemorrhoid and establishes a predetermined current time unit;
    contacting said hemorrhoid with a probe of the current delivering medical instrument whereby the medical instrument includes
        a base unit; and
        a handpiece which includes
            a speaker;
            a lower handle portion from which extends a connector cord to the base unit; and
            a planar face surface including
                a display for displaying visual indicators including a current time unit;
                a level of treatment current indicator for displaying current level of treatment; and
                a circuit status indicator;
    the medical instrument configured to monitor the cumulative current and time of a treatment session;
    delivering current to the hemorrhoid,
    determining a delivered current time unit, said delivered current time unit comprising a product comprised of current delivered multiplied by time, said medical instrument being configured to provide an indication when the predetermined current time unit amount is achieved.

7. The method of claim 6 where the indication when a predetermined current time unit amount is achieved is a visual indication provided on the display.

8. The method of claim 6 where the indication when a predetermined current time unit amount is achieved is an audible indication provided through the speaker.

* * * * *